United States Patent [19]

Christie et al.

[11] Patent Number: 5,277,701
[45] Date of Patent: Jan. 11, 1994

[54] TREATMENT OF ALUIMMUNIZATION AND REFRACTORINESS TO PLATELET TRANSFUSION BY PROTEIN A COLUMN THERAPY

[75] Inventors: Douglas J. Christie, St. Paul; Robert B. Howe, Wayzata, both of Minn.

[73] Assignee: Regents of the University of Minnesota, Minneapolis, Minn.

[21] Appl. No.: 792,814

[22] Filed: Nov. 15, 1991

[51] Int. Cl.$^5$ ............................................. A61M 37/00
[52] U.S. Cl. ................................................... 604/4
[58] Field of Search ............................. 604/5, 4, 52, 53

[56] References Cited

U.S. PATENT DOCUMENTS

| 5,041,079 | 8/1991 | Takashima et al. | 604/5 |
| 5,061,237 | 10/1991 | Gessler et al. | 604/5 |
| 5,104,373 | 4/1992 | Davidner | 604/5 |

FOREIGN PATENT DOCUMENTS 0056977  8/1982  European Pat. Off. ............... 623/5

OTHER PUBLICATIONS

Christie et al., "Treatment of Refractoriness to Platelet Transfusion by Protein A Column Therapy", *Transfusion*, 33:234-242 (1993).

Jones et al., "Selective Extracorporeal Removal of Immunoglobulin-G and Circulating Immune Complexes: A Review", *Plasma Ther. Transfus. Technology*, 7:333-349 (1986).

McGrath et al., "Transient Platelet and HLA Antibody Formation in Multitransfused Patients with Malignancy", *British Journal of Hematology*, 68:345-350 (1988).

Messerschmidt et al., "The Status of Plasma Therapy as Cancer Treatment", *Journal of Clinical Oncology* 6:189-212 (1988).

Andreu et al., "Prevention of HLA immunization with leukocyte-poor packed red cells and platelet concentrates obtained by filtration", *Blood*, 72:964 (1988).

Andreu et al., "Ultraviolet irradiation of platelet concentrates: Feasibility in transfusion practice", *Transfusion*, 30:401 (1990).

Bensinger et al., "Plasma exchange for platelet alloimmunization", *Transplantation*, 41:602 (1986).

Berndt et al., "Additional glycoprotein defects in Bernard-Soulier's syndrome: Confirmation of genetic basis by parental analysis", *Blood*, 62:800 (1983).

Boizard et al., "Lek$^a$, a new platelet antigen absent in Glanzmann's thrombasthenia", *Vox Sang*, 46:47 (1984).

Brand et al., "Alloimmunization after leukocyte-depleted multiple random donor platelet transfusions", *Vox Sang*, 54:160 (1988).

Branda et al., "Immunoadsorption of human plasma with protein A-sepharose columns", *Transfusion*, 26:471 (1986).

Christie et al., "Detection of drug-dependent platelet antibodies using immobilized Staphylococcal protein A", *Transfusion*, 28:322 (1988).

(List continued on next page.)

*Primary Examiner*—David Isabella
*Attorney, Agent, or Firm*—Merchant, Gould, Smith, Edell, Welter & Schmidt

[57] ABSTRACT

The invention provides a therapeutic method for treating refractoriness to platelet transfusion by isolating blood serum from an alloimmunized patient undergoing platelet transfusion therapy, passing the serum through a bed comprising staphococcal protein A coupled to a solid support and returning the treated plasma to the patient. The method can be conducted by batch-type procedure or by continuously conducting the steps so that blood is withdrawn, passed through the bed, and returned to the patient as a continuous stream. The method is useful to treat alloimmunized patients suffering from leukemia, aplastic anemia, myelofibrosis, myelodysplastic syndrome, or in a bone marrow transplant patient.

7 Claims, 3 Drawing Sheets

OTHER PUBLICATIONS

Christie et al., "Vancomycin-dependent antibodies associated with thrombocytopenia and refractoriness to platelet transfusion in patients with leukemia", *Blood*, 75:518 (1990).

Cimo et al., "Detection of drug-dependent antibodies by the $^{51}$Cr platellet lysis test: Documentation of immune thrombocytopenia induced by diphenylhydanoin, diazepam and sulfisoxazole", *Am. J. Hematol.*, 2:65 (1977).

Coller et al., "A murine monoclonal antibody that completely blocks the binding of fibrinogen to platelets produces a thrombasthenic-like state in normal platelets and binds to glycoproteins IIb and/or IIIa", *J. Clin. Invest.*, 72:325 (1983).

Coller et al., "Evidence that glycocalicin circulates in normal plasma", *J. Clin. Invest.*, 73:794 (1984).

Daly et al., "Platelet transfusion therap. One-hour post-transfusion increments are valuable in predicting the need for HLA-matched preparations", *JAMA*, 253:435 (1980).

Deeg, "Transfusions with a tan-Prevention of allosensitization by ultraviolet irradiation", *Transfusion*, 29:450 (1989).

Eernisse et al., "Prevention of platelet refractoriness due to HLA antibodies by administration of leukocyte--poor blood components", *Exp. Hematol.*, 9:77 (1981).

Furihata et al., "On the association of the platelet-specific alloantigen, Pen$^a$, with glycoprotein IIIa. Evidence for heterogeneity of glycoprotein IIIa", *J. Clin. Invest.*, 80:1624 (1987).

Gurthrie, et al., "Immune thrombocytopenia purpura: A pilot study of staphylococcal protein A immunomodulation in refractory patients", *Seminars in Hematology*, 26(Suppl 1):3 (1989).

Herman et al., "Platelet transfusion. Current techniques, remaining problems, and future prospects", *Am. J. Ped. Hematol/Oncol.*, 9:272 (1987).

Hogge et al., "Lymphocytotoxic antibody is a predictor of response to random donor platelet transfusion", *Am. J. Hematol.*, 14:363 (1983).

Hogge et al., "The ineffectiveness of random donor platelet transfusion in splenectomized, alloimmunized recipients", *Blood*, 64:253 (1984).

Ikeda et al., "A new platelet-specific antigen, Nak$^a$, involved in the refractoriness of HLA-matched platelet transfusion", *Vox Sang*, 57:213 (1989).

Jones et al., "Ultraviolet irradiation of platelet concentrate abrogates lymphocyte activation without affecting platelet function in vitro", *Plasma Ther. Transfus. Technol.*, 7:333 (1987).

Kahn et al., "Selective extracorporeal removal of immunoglobulin-G and circulating immune complexes: a review", *Transfusion*, 25:547 (1985).

Kakaiya et al., "Four crossmatch methods to select platelet donors", *Transfusion*, 24:35 (1984).

Kelton et al., "Gov$^{a/b}$ alloantigen system of human platelets", *Blood*, 75:2172 (1990).

Kickler et al., "The predictive value of crossmatching platelet transfusions for alloimmunized patients", *Transfusion*, 25:385 (1985).

Kickler et al., "Alloimmunization to platelet-specific antigens on glycoproteins IIb-IIIa and Ib/IX in multiply transfused thrombocytopenic pateints", *Transfusion*, 30:622 (1990).

Kiefel et al., "Monoclonal antibody-specific immobilization of platelet antigens (MAIPA): A new tool for identification of platelet-reactive antibodies", *Blood*, 70:1722 (1987).

Kunicki et al., "Isolation and immunologic characterization of the human platelet alloantigen, Pl$^{A1}$", *Mol. Immunol.*, 16:353 (1979).

Langenscheidt et.al., "Platelet transfusion refractoriness associated with two rare platelet specific alloantibodies (anti-Bak$^a$ and anti-Pl$^{A2}$) and multiple HLA antibodies", *transfusion*, 28:597 (1988).

Lazzarino et al., "Cyclosporine in the treatment of aplastic anemia and pure red-cell aplasia", *Bone Marrow Transplant.*, 4 (Suppl 4):165 (1989).

Litzow et al., "Multiple responses of a plastic anemia to low-dose cyclosporine therapy despite development of a myelodysplastic syndrome", *Am. J. Hematol.*, 32:226 (1989).

McCullough et al., "Platelet utilization in a university hospital", *JAMA*, 259:2414 (1988).

Messerschmidt et al., "Protein A immunoadsorption in the treatment of malignant disease", *J. Clin. Oncol.*, 6:203 (1988).

Miller et al., "Antithymocyte globulin treatment of severe aplastic anaemia", *Brit. J. Haematol.*, 55:17 (1983).

Mittleman et al., "Treatment of patients with HIV thrombocytopenia and hemolytic uremic syndrome with protein A (Prosorba ® Column) immunoadsorption", *Seminars in Hematology*, 26 (Suppl 1):15 (1989).

Muroi et al., "The effect of immunoadsorption therapy by a protein A column on patients with thrombocytopenia", *Seminars in Hematology*, 26 (Suppl 1):10 (1989).

Murphy et al., "Immunological aspects of platelet transfusions", *Brit. J. Haematol.*, 60:409 (1985).

Murphy et al., "Use of leucocyte-poor blood components and HLA-matched-platelet donors to prevent HLA alloimmunization", *Brit. J. Haematol.*, 62:529 (1986).

Newman et al., "Quantitation of membrane glycoprotein IIIa on intact human platelets using the monoclonal antibody, AP-3", *Blood*, 65:227 (1985).

O'Connell et al., "The value of 10-minute posttransfusion platelet counts", *Transfusion*, 28:66 (1988).

Reed et al., "Effect of antiidiotypic antibodies to HLA on graft survival in renal-allograft recipients", *New Engl. J. Med.*, 316:1450 (1987).

Saarinen et al., "Effective prophylaxis against platelet refractoriness in multitransfused patients by the use of leukocyte-free blood components", *Blood*, 75:512 (1990).

Saji et al., "New platelet antigen, Sib$^a$, involved in platelet transfusion refractoriness in a Japanese man", *Vox Sang*, 56:283 (1989).

Schiffer et al., "High dose intravenous gammaglobulin in alloimmunized platelet transfusion recipients", *Blood*, 64:937 (1984).

Schiffer, "Prevention of alloimmunization against platelets", *Blood*, 77:1 (1991) (editorial).

Snyder et al., "Reduction in platelet-binding immunoglobulins and improvement in platelet counts in patients with HIV-associated idiopathic thrombocytopenia purpura (ITP) following extracorporeal immunoadsorption of plasma over staphylococcal protein A-silica", *Artif. Organ.*, 13:71 (1989).

van Marwijk et al., "Use of leukocyte-depleted platelet concentrates for the prevention of refractoriness and primary HLA alloimmunization: A prospective, randomized trail", *Blood*, 77:201 (1991).

TREATMENT OF ALUIMMUNIZATION AND REFRACTORINESS TO PLATELET TRANSFUSION BY PROTEIN A COLUMN THERAPY

BACKGROUND OF THE INVENTION

The present invention was made with the support of the National Institutes of Health under Grant No. 1R01-HL-44917-01. The Government has certain rights in the invention.

Refractoriness to platelet transfusion (RPT) is a serious complication of leukemia therapy, bone marrow transplantation, and other disorders where multiple infusions of platelets are required to prevent bleeding. Alloimmunization to HLA class I antigens is an important cause of RPT, with some estimates as high as 50–70% of patients receiving multiple platelet transfusions becoming alloimmunized to HLA antigens. (P. Daly et al., *JAMA*, 253:435 (1980); D. Hogge et al., *Am. J. Hematol.*, 14:363 (1983); R. Kakaiya et al., *Transfusion*, 24:35 (1984); J. Eernisse et al., *Exp. Hematol.*, 9:77 (1981); M. Murphy et al., *Brit. J. Haematol.*, 60:409 (1985); and M. Murphy et al., *Brit. J. Haematol.*, 62:529 (1986).) Additionally, antibodies directed against platelet-specific antigens, such as HPA-1a(=Pl$^{A1}$)*, HPA-1b(=Pl$^{A2}$) and HPA-3a(=Bak$^a$), HPA-2b(=Sib$^a$), Nak$^a$, and Gov$^a$/Gov$^b$ have also been implicated in platelet transfusion failure. (R. Kickler et al., *Transfusion*, 30:622 (1990); F. Langenscheidt et al., *Transfusion*, 28:597 (1988); H. Saji et al., *Vox Sang*, 56:283 (1989); H. Ikeda et al., *Vox Sang*, 57:213 (1989); and J. Kelton et al., *Blood*, 75:2172 (1990).) Moreover, drug-dependent antibodies induced by vancomycin were recently found in association with RPT in two patients with leukemia. (D. Christie et al., *Blood*, 75:518 (1990).) Thus, it is apparent that a wide variety of different antibodies may contribute to shortened survival of transfused platelets.

Standard transfusion strategies generally recommend that patients first receive pooled random donor platelets, followed by random single donor and HLA-matched single donor platelets once alloimmunization occurs. (J. Herman et al., *Am. J. Ped. Hematol./Oncol.*, 9:272 (1987)). Although steroids, splenectomy, immunosuppressive therapy, IV IgG, and plasmapheresis have often proved successful in treating autoimmune thrombocytopenia (ATP), they have for the most part been ineffective in reducing RPT due to alloimmunization. (J. Herman et al., *Am. J. Ped. Hematol./Oncol.*, 9:272 (1987); D. Hogge et al., *Blood*, 64:253 (1984); C. Schiffer et al., *Blood*, 64:937 (1984); and W. Bensinger et al., *Transplantation*, 41:602 (1986).) Several reports have shown marked increases in platelet counts in patients with ATP following reinfusion of autologous plasma that had been absorbed by immobilized protein A. (T. Guthrie et al, *Sem. Hematol.*, 26(Suppl 1):3 (1989); K. Muroi et al., *Sem. Hematol.*, 26(Suppl 1):10 (1989); A. Mittleman et al., *Sem. Hematol.*, 26(Suppl 1):15 (1989); and H. Snyder, Jr. et al., *Artif. Organ*, 13:71 (1989).) In the present study, we investigated the effectiveness of protein A column therapy for improving platelet counts and transfusion refractoriness in 12 thrombocytopenic patients with histories of being unresponsive to platelet transfusion therapy.

SUMMARY OF THE INVENTION

A therapeutic method is provided for treating refractoriness to platelet transfusion (RTP) in alloimmunized patients undergoing platelet transfusion therapy which permits the patients to sustain higher average daily platelet counts (2–10X higher than pretreatment) and to exhibit improved responsiveness to both random and HLA-matched platelet transfusion. The present method also decreases circulating platelet antibodies, which are responsible for alloimmunization.

Generally, the present method comprises:

(a) isolating a portion of blood serum, i.e., about 500–2500 ml of plasma, from an alloimmunized patient undergoing platelet transfusion therapy;

(b) passing the portion of serum through a bed comprising Staphylococcal protein A immobilized on a solid support (i.e., coupled to silica gel or to another particulate inorganic oxide) so that immunoglobulin (IgG) and, preferably, IgG-associated immune complexes are removed from the serum, to yield a portion of treated plasma; and (c) returning said portion of treated plasma to the patient.

RTP is commonly exhibited by alloimmunized patients suffering from leukemia, aplastic anemia, myelofibrosis, myelodysplasia or bone marrow transplant patients. Typically, the bed of immobilized protein A is packed into a chromatography column, and about 500–2500 ml of plasma per treatment, is passed through the column. The 500–2500 ml portion, or other portion of blood plasma is typically obtained by withdrawal of serial units of blood from the patient undergoing transfusion therapy, centrifuging the units to separate the blood into the plasma and the cellular portion, pooling the plasma to yield said plasma portion, and returning the cellular component to the patient. The method can be operated in a "batch" fashion, i.e., in discrete steps, or steps (a) to (c) above can be performed continuously. For example, a stream of blood is removed from the patient, centrifuged to separate a plasma stream from the cellular component, the plasma stream can be passed through a column packed with $SiO_2$-immobilized protein A, and the resultant treated plasma stream can be recombined with the cellular component and reinfused into the patient.

DETAILED DESCRIPTION OF THE INVENTION

Figure 1A:
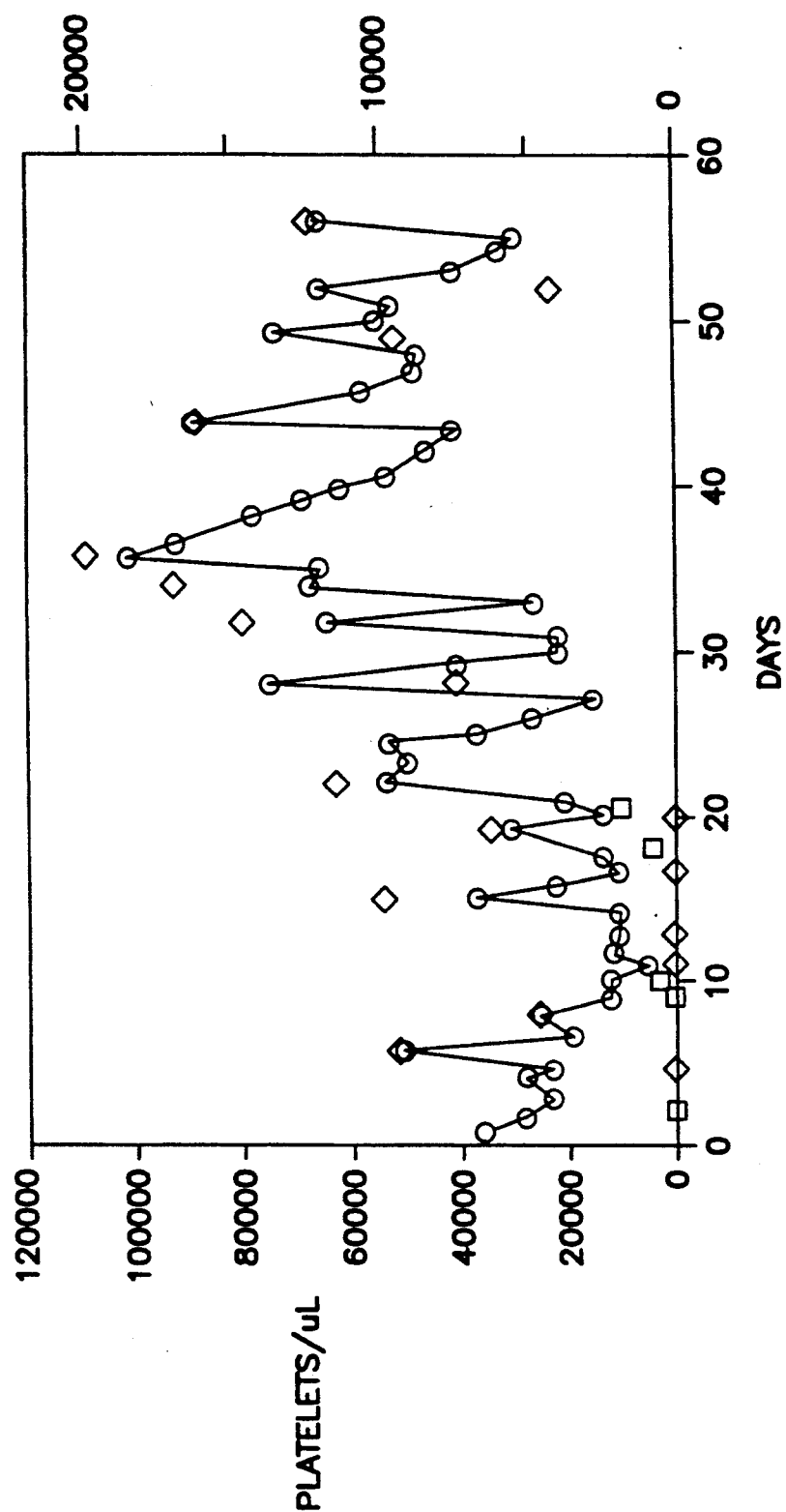
FIGS. 1A and 1B: Average daily best platelet counts (circles) and posttransfusion CCI from random donor platelets (open squares) or HLA matched platelets (closed squares) measured at 10–120 min (or occasionally >2 h and <24 h) before, during, and after protein A column treatments (arrows) in patients No. 4 and 7. CCI <7500 (horizontal line) were below levels acceptable for successful transfusions. All CCI measured at >2 h were <4500. Each CCI value represents the best response to a single platelet transfusion for that day, although other transfusions may have been given on the same day. Patient No. 4 received a five-day course of cyclosporin A (CSA) beginning with the fourth protein A column treatment.

Twelve thrombocytopenic patients (platelets <10-24×10$^9$/L) were investigated for their responsiveness to staphylococcal protein A column therapy. All patients had bone marrow failure with diagnoses including leukemia, aplastic anemia, myelofibrosis, and myelodysplastic syndrome. Ten patients had previously been treated with steroids, intravenous gammaglobulin (IV IgG), and/or other forms of immunosuppressive therapy without response. All patients were receiving multiple platelet transfusions without achieving one hour corrected count increments (CCI) $\geq$7500. Ten patients had platelet antibodies directed against HLA class I antigens, ABO antigens, and/or platelet-specific antigens as detected by immunofluorescence, monoclonal antibody antigen-capture ELISA, and/or lymphocytotoxicity. The other two patients had no detectable platelet antibodies by these methods.

Plasma (500-2000 mL) was passed over a protein A silica gel column (Prosorba®, IMRE Corp., Seattle, Wash.) then reinfused into the patient. Patients typically received six treatments (range=1-14). A positive response to protein A therapy was defined as at least a doubling of the pretreatment platelet count and/or two successive 10 to 120-minute posttransfusion CCI$\geq$7500. Following plasma treatments, 7/12 patients responded with daily platelet counts that averaged 62$\pm$21×10$^9$/L (range=46 to >100×10$^9$/L) as compared with 14$\pm$8×10$^9$/L (range= <10 to 24×10$^9$/L) before treatment. Posttransfusion CCI values determined among four of these patients averaged 1900$\pm$700 and 11,800$\pm$3900 before and after treatment, respectively. In contrast, among the five nonresponders pre- and post-treatment platelet counts averaged 9$\pm$8×10$^9$/L (range= <10 to 23×10$^9$/L) and 11$\pm$9×10$^9$/L (range= <10 to 25×10$^9$/L), respectively, while posttransfusion CCI were 600$\pm$1300 and 1100$\pm$2200, respectively.

Following protein A column treatments, seven of these patients achieved transient (1-2 week) to long term (>6 month) increases in platelet counts that in six patients (Patient No. 5 no longer being transfused) were accompanied by improved responsiveness to platelet transfusions. For most of these patients, the improvement in post-transfusion platelet increments was accompanied by decreased platelet usage, although two non-responders also utilized fewer platelets following treatment. All six responders with detectable platelet antibodies had measurable reductions in the titers and/or specificities of these antibodies after protein A therapy while two non-responders demonstrated similar declines in these antibodies.

Other factors investigated included the effect of protein A treatments on platelet usage and platelet antibody levels. Protein A column treatments also were associated with decreased platelet usage of 15-65% in 5/7 responders and 1/5 nonresponders. For most of these patients the improvement in posttransfusion platelet increments was accompanied by decreased platelet usage, although two nonresponders also utilized fewer platelets following treatment. Of the six responders with detectable platelet antibodies, all had a reduction of 40 to >95% in the level of these antibodies following protein A treatment. Only one nonresponder had a similar reduction in platelet antibody level. These findings suggest that in certain patients with refractoriness to platelet transfusion due to platelet alloantibodies, protein A column treatments may be an effective means of increasing platelet counts and posttransfusion CCI, reducing platelet usage, and reducing levels of circulating platelet antibodies.

In two previous studies, an alloimmunized patient with aplastic anemia and one with acute myelogenous leukemia, demonstrated improved response to platelet transfusion following protein A column treatments, although three other alloimmunized patients with RPT failed to respond to platelet transfusion following similar therapy. (K. Muroi et al., Sem. Hematol, 26(Suppl 1):10 (1989); R. Branda et al., Transfusion, 26:471 (1986); and K. Muroi et al., Sem. Hematol, 26(Suppl 1):10 (1989).) Other than these reports, we are aware of no other studies that have investigated the potential medical benefit of protein A column therapy in the treatment of alloimmunized patients with RPT.

In this study, patients received from 1-14 protein A column treatments. This study does not address the optimum number of treatments that will result in a clinically meaningful benefit to the patient. However, it is clear from our results that as few as one or two columns was associated with markedly increased platelet counts and posttransfusion CCI (Table 2), which in some patients (FIG. 1) may have involved increased endogenous platelet production and/or increased survival of transfused platelets. Moreover, 25-50% of 96 patients with ATP who presented with average platelet counts <30×10$^9$/L responded after only one or two Prosorba® treatments with increased platelet counts averaging >130×10$^9$/L (personal communication, Dr. Harry Snyder, Seattle, Wash., February 1991).

Due to the use of concurrent alternate forms of immunosuppressive therapy in five of the responders (Table 2), we cannot conclude with certainty that protein A column therapy alone is effective in the treatment of alloimmunized patients with RPT. However, none had previously responded to these therapies with increased platelet counts, increased posttransfusion CCIs, or decreased transfusion requirements. Moreover, only one responder (No. 4, Tables 1 and 2) received additional immunosuppressive agents during protein A treatment that had not been administered before hand. This patient was given ATG 25 days before protein A therapy followed by cyclosporin between the 4th and 6th protein A column treatments that appeared to correlate with an almost immediate (24-48 h) improvement in posttransfusion CCI values (Table 2). However, it seems unlikely that this was a direct effect of either the ATG or the cyclosporin because the response time for these agents in aplastic anemia is 2-9 months. (W. Miller et al., Brit. J. Haematol., 55:17 (1983); M. Litzow et al., Am. J. Hematol., 32:226 (1989); and M. Lazzarino et al., Bone Marrow Transplant, 4(Suppl 4):165 (1989).) The present study strongly suggests that protein A therapy played a role in the improved platelet transfusion outcome in these patients.

The mechanism of action of protein A column therapy is poorly understood. However, it does not appear to be related solely to the removal from plasma of circulating platelet antibodies because removal of <5% of circulating IgG by protein A treatments is associated with remission in patients with ATP and malignancies. (F. Jones et al., Plasma Ther. Transfus. Technol., 7:333 (1987) and G. Messerschmidt et al., J. Clin. Oncol., 6:203 (1988).) Patients No. 2 and 10 lacked detectable platelet antibodies and yet failed in response to platelet transfusion despite lack of evidence for obvious nonimmunologic factors, such as disseminated intravascular coagulation, splenomegaly, or sepsis, to account for platelet consumption. Others have similarly reported transfusion failure in apparently antibody-negative patients with RPT, and conversely, occasionally observed patients responding to platelet transfusion despite the presence of circulating platelet-reactive antibodies. (D. Hogge, Am. J. Hematol., 14:363 (1983) and D. Hogge et al., Blood, 64:253 (1984).) Nevertheless, after protein A treatment Patient No. 2 achieved increased platelet counts, while Patient No. 10 did not (Table 2). Recent observations in 3/13 apparently antibody-negative patients with ATP who responded to protein A therapy support our findings (personal communication, Dr. Harry Snyder, Seattle, Wash., May 1991). However, all patients with detectable platelet antibodies who achieved increased platelet counts and responsiveness to transfusion after protein A treatments had decreased titers in platelet alloantibodies, although two patients (Nos. 8 and 12) who had a similar reduction in platelet antibodies failed to respond to transfusion. Thus, the mechanism of protein A action may not directly involve reduction in the level of circulating platelet antibodies.

Recently, HIV infected patients with ATP, who were treated with protein A therapy, were found to possess anti-F(ab')$_2$ antibodies directed against platelet autoantibodies. (H. Snyder Jr. et al., Artif. Organ, 13:71 (1989).) The presence of anti-F(ab')$_2$ antibodies in these patients was associated with reduced levels of circulating platelet antibodies and platelet-associated immunoglobulins and increased endogenous platelet production. It is of interest to note that the presence of circulating antiidiotypic antibodies to HLA antigens has been associated with graft survival among renal transplant patients, while the presence of antibodies potentiating HLA antibodies correlated with graft rejection. (E. Reed et al., N. Enq. J. Med., 316:1450 (1987).) One speculation then may be that in patients who have been sensitized to HLA and platelet-specific antigens and who are refractory to platelet transfusion, protein A column therapy promotes production of antiidiotypic antibodies to these platelet-reactive antibodies, thus neutralizing their anti-platelet activity.

Ideally, prevention of alloimmunization should greatly reduce the incidence of RPT in multiply transfused recipients. In fact several reports indicate that reduction in alloimmunization and RPT may be accomplished by transfusing red blood cells and platelets that have been depleted of contaminating leukocytes. (J. Eernisse et al., Exp. Hematol., 9:77 (1981); A. Brand et al., Vox Sang, 54:160 (1988); G. Andreu et al., Blood, 72:964 (1988); I. Sniecinski et al., Blood, 71:1402 (1988); U. Saarinen etc al., Blood, 75:512 (1990); and M. van Marwijk Kooy et al., Blood, 77:201 (1991). Other studies indicate that UV-B irradiation of lymphocytes present in transfused blood components may also be an effective method for reducing alloimmunization. (R. Kahn et al., Transfusion, 25:547 (1985); H. Deeg, Transfusion, 29:450 (1989); and G. Andreu et al., Transfusion, 30:401 (1990). However, as suggested by a recent editorial, these procedures are unlikely to reduce or eliminate the problem of alloimmunization in transfusion recipients previously sensitized to platelet antigens. (C. Schiffer, Blood, 77:1 (1991).) Thus, the need for treatment of alloimmunized patients will be an ongoing requirement.

In summary, use of IV IgG, splenectomy, immunosuppressive agents, and apheresis, often found to be effective in the treatment of refractory ATP, have generally failed or had limited utility in the reduction of RPT due to alloimmunization. (J. Herman et al., Am. J. Ped. Hematol./Oncol., 9:272 (1987); D. Hogge et al., Blood, 64:253 (1984); C. Schiffer et al., Blood, 64:937 (1984); and W. Bensinger et al., Transplantation, 41:602 (1986).) Clearly then, an effective means to manage- the alloimmunized patient who is unresponsive to platelet transfusion is needed. Our findings strongly suggest that some alloimmunized patients with RPT may benefit from treatment of their plasma with immobilized protein A. Specifically, our study indicates that in certain patients protein A column therapy may be safe and effective for increasing platelet counts and posttransfusion increments, reducing platelet usage, and reducing levels of circulating platelet-reactive alloantibodies.

EXAMPLE

Patients

Patients were recruited for this study by the following criteria: 1) platelet count $<30 \times 10^9/L$;2) refractory to platelet transfusion as defined by failure to achieve a 10–60 min posttransfusion corrected count increment (CCI) $\geq 7500$ following two successive transfusions; 3) diagnosis consistent with bone marrow failure; and 4) evidence of alloimmunization to platelet antigens. (T. Kickler et al., Transfusion, 25:385 (1985) and B. O'Connell et al., Transfusion, 28:66 (1988).) By this criteria, 12 patients were enrolled in this study between November 1989 and September 1991. All patients gave informed consent in accordance with guidelines established by the University of Minnesota Committee on Use of Human Subjects in Research. Specific diagnoses and other relevant patient information are listed in Table 1.

TABLE 1

PATIENT INFORMATION

| Patient No. | Age | Sex | Diagnosis* | Clinical Outcome | Platelet Count ($\times 10^9/L$) | Prior§ Treatment | Antibody Specificity |
|---|---|---|---|---|---|---|---|
| 1 | 19 | M | AA | discharged | 17 | ATG/CT | α-HLA |
| 2 | 49 | F | CML | expired (3 wk) | 24 | CT (22) | Not detected** |
| 3 | 20 | M | MDS/BMT | expired (3 days) | <10 | CT/ATG/ALG/IgG | α-HLA |
| 4 | 70 | F | AA | discharged | 23 | ATG/CT (12) | α-A(IgG) |
|   |   |   |   |   |   |   | α-HLA(IgG) |
| 5 | 61 | M | CMML | discharged | 13 | None | α-HLA(IgG) |
|   |   |   |   |   |   |   | α-HPA-1a(IgG) |
|   |   |   |   |   |   |   | α-HPA-3a(IgG) |
| 6 | 12 | F | AA/BMT | discharged | <10 | CT/IgG (12) | α-HLA(IgG + IgM) |
|   |   |   |   |   |   |   | α-GPIb/IX(IgM) |
|   |   |   |   |   |   |   | α-GPIIb/IIIa(IgM) |
| 7 | 48 | F | MDS | expired (8 days) | 11 | CT/IgG (18) | α-HLA(IgG) |
| 8 | 35 | M | AML/BMT | discharged | <10 | CT/IgG | α-HLA(IgG + IgM) |

TABLE 1-continued

PATIENT INFORMATION

| Patient No. | Age | Sex | Diagnosis* | Clinical Outcome | Platelet Count ($\times 10^9$/L) | Prior§ Treatment | Antibody Specificity |
|---|---|---|---|---|---|---|---|
| 9 | 54 | M | MF | expired (1 day) | <10 | CT/IgG | α-HLA |
| 10 | 20 | M | ALL | expired (11 mo) | 23 | CT (31) | Not detected |
| 11 | 68 | M | MF | expired (4 wk) | <10 | CT/IR (9) | α-HLA(IgG) |
| 12 | 36 | F | AML | expired (7 days) | <10 | None | α-HLA(IgG) |

*Abbreviations are: AA, aplastic anemia; ALL, acute lymphocytic leukemia; CML, chronic myelogenous leukemia; CMML, chronic myelomonocytic leukemia; MDS, myelodysplastic syndrome; and MF, myelofibrosis. Three patients (Nos. 3, 6 and 8) were bone marrow transplant recipients (BMT).

Seven patients expired (EXP) from complications of their primary diagnoses at various times following protein A column treatment, which did not contribute to any of the causes of death.

Average best daily posttransfusion (10-120 min) platelet count from the onset of RPT during the last admission and before starting protein A column therapy, which ranged from 4 to 23 days.

§ For thrombocytopenia and RPT during last admission: ATG, antithymocyte globulin; CT, chemotherapy (steroids, vinca alkaloids, cyclophosphamide, azathioprine); IgG, intravenous gammaglobulin; IR, irradiation of spleen. The number in parentheses indicates the days patient was unresponsive to therapy from the time of the last admission. In some case this information was unavailable.

Platelet-reactive antibody studies were performed with sera collected immediately prior to the beginning of protein A column therapy. Antibodies reacted with antigens of the ABO system (A), human leukocyte antigen system (HLA), human platelet antigen system [HPA:HPA-1a(=P1[41]) and HPA-3a(=Bak[a])], and unidentified epitopes of various platelet glycoproteins (GP). In most but not all cases, immunoglobulin class was determined and noted in parentheses.

**No antibodies were detected by PIFT, MAIPA, or lymphocytotoxicity.

Platelet Transfusions

Patients received platelet transfusions in accordance with general practices and guidelines approved by the University of Minnesota Hospital Transfusion Therapeutics Committee. (J. McCullough et al., *JAMA*, 259:2414 (1988).) Where possible, successful transfusions were judged by the criteria described above, although the posttransfusion time was occasionally extended to 120 min. or longer but not more than 24 hr.

Protein A column therapy

The PROSORBA ® column is marketing approved by the United States Food and Drug Administration (FDA) for use in the therapeutic removal of immunoglobulin G (IgG) and IgG-containing circulating immune complexes (CIC) from plasma of patients with ITP having platelet counts less than 100,000/mm³. ITP is an autoimmune disease that afflicts about 25,000 Americans with approximately 2,500 new cases annually. ITP occurs in the general population but also is present in approximately 10% of HIV antibody-positive individuals.

Protein A is a major component of certain strains of *Staphylococcus aureus* (SAC). Protein A has a propensity to bind IgG via the Fc portion and has even greater affinity for IgG bound to an antigen (i.e. CIC). When protein A is a part of a solid matrix, either as a component of the SAC or when it is isolated from SAC and bound to an inert substance, it can be used as an effective reagent for the removal of IgG or CIC from plasma. The use of protein A as an immunological reagent has been studied in great detail, due to its applicability to the specific isolation of immunoglobulins and/or immunoglobulin bound antigens.

The PROSORBA column employs 200 mg of protein A which has been covalently bound to an inert silica matrix. The protein A-silica is contained within a biocompatible, polycarbonate assembly which is designed for the sterile passage of plasma. Plasma can thus be exposed to the protein A with subsequent adsorption of IgG and CIC. Treated plasma which has passed through the device can then be returned to the patient.

This medical treatment device was approved for market distribution by the FDA on Dec. 23, 1987 as follows: The PROSORBA ® column is indicated for use in the therapeutic removal of immunoglobulin G (IgG) and IgG-containing circulating immune complexes (CIC) from plasma in patients with idiopathic thrombocytopenic purpura having platelet numbers less than 100,000/mm³.

A. Column Preparation

1. Standard aseptic technique must be used for all PROSORBA ® column tubing connections.

2. Fluid flowing through the PROSORBA ® column must always be directed upward (i.e., fluid must enter the PROSORBA ® column at the base inlet and exit at the top outlet).

3. Prime the PROSORBA ® column with a wash of 4.0 liters of 0.9% sterile saline (IV quality). To remove trapped air and to ensure maximum wash efficiency, use the following steps: (a) fill the column with saline; (b) interrupt the flow; and (c) rotate the column slowly and gently to completely wet the matrix prior to passing the rest of the sterile saline through the column. Do not allow air to enter the column.

4. When the wash is complete, anticoagulate the column by passing an additional ½ liter of 0.9% sterile sale (IV quality) containing 5,000 units of sodium heparin through the column at 20 ml/min.

5. Do not disturb the PROSORBA ® column during the final 3.5 liters of sterile saline prime or during the anticoagulation procedure.

B. On-Line Preparation

1. Prepare the apheresis apparatus as indicated in the apparatus manufacturer's instructions, including establishment of patient blood access and anticoagulation.

2. Attach the washed, anticoagulated PROSORBA ® column (see Column Preparation—VIII.A. above) in an upright position to the plasma return line of the apheresis apparatus. Plasma flow must be directed upward through the column.

3. Initiate apheresis apparatus operation discarding the first 250 ml of fluid (0.9% saline +5,000 units of sodium heparin) from the column to the waste container.

4. Reestablish plasma flow back into the patient and perfuse the prescribed plasma volume (up to 2,000 ml) through the PROSORBA ® column at 10-20 ml/min.

5. Terminate the plasma perfusion with the following steps: (a) displace the plasma remaining in the column with 250 ml of sterile IV quality 0.9% saline; (b) infuse the displaced plasma into the patient at 10-20 ml./min.; and (c) disconnect the patient from the apheresis apparatus as indicated in the manufacturer's instructions.

6. Vital signs should be monitored at the initiation of the PROSORBA ® column treatment and at least every 30 minutes during the procedure. The patient also should be monitored for a period of time after the treatment has been terminated.

Plasma from each patient was passed over a staphylococcal protein A silica gel column (the PROSORBA ® immunoadsorption treatment column, IMRE Corp., Seattle, Wash.) by either an on-line or off-line technique as directed by the manufacturer. For the on-line procedure, whenever possible, a minimum of 1500 mL of plasma were treated per protein A column utilizing CS 3000 apheresis equipment (Baxter, Deerfield, Ill.) to collect the plasma. For the off-line procedure, a minimum of 500 mL of plasma were treated per protein A column, where plasma was obtained by centrifugation of two units of whole blood. Following protein A treatment, the plasma was returned to the patient who received additional column treatments at intervals of 2-3 days. The other blood components obtained from each procedure were reinfused prior to return of the treated plasma. Standard protocols for protein A column therapy utilize six column treatments. The actual number of treatments received by each patient are shown in Table 2.

2) following treatment, patients had to achieve at least two successive one-hour posttransfusion CCI $\geq 7500$.

(H. Snyder Jr. et al., *Artif. Organ*, 13:71 (1989).) Patients fulfilling either of these criteria were considered to have a positive response to protein A therapy.

Figure 1B:
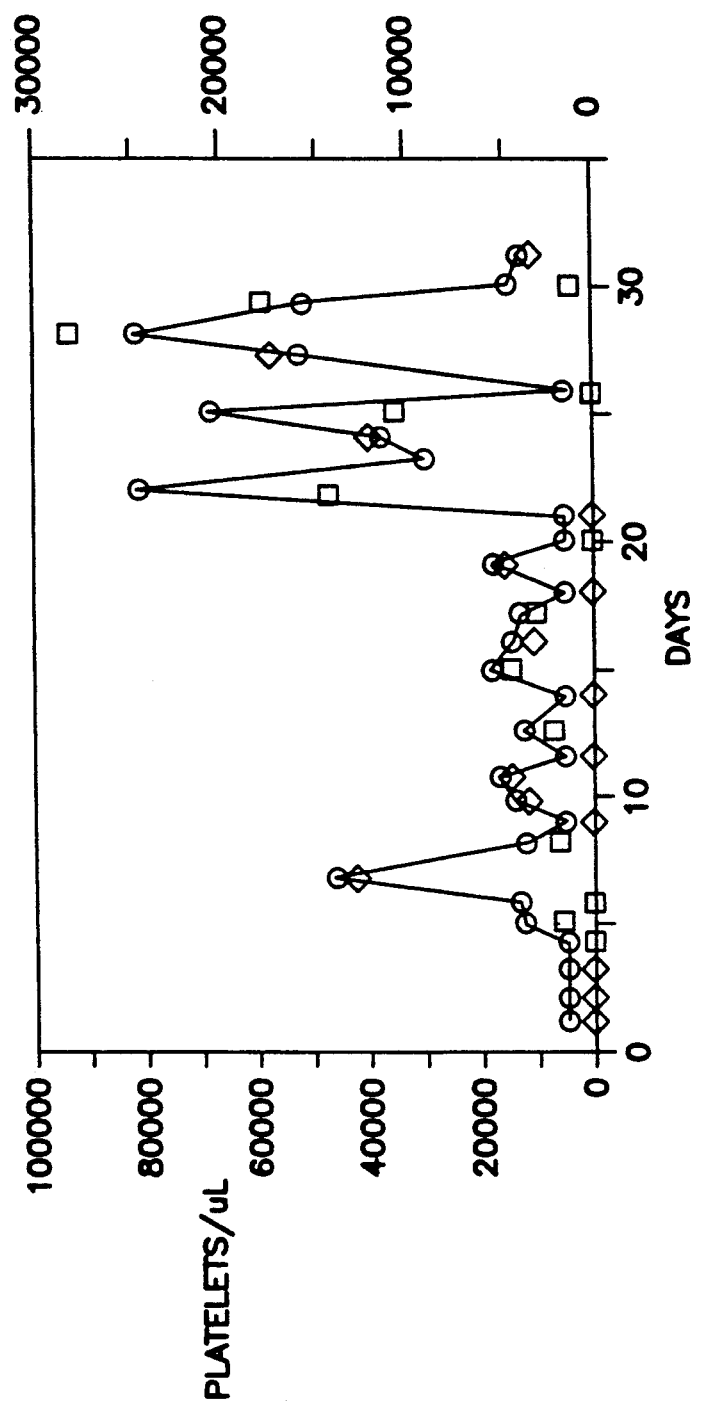

Changes in platelet counts and posttransfusion CCI before, during, and after protein A column therapy are shown for Patients No. 4 and 7 in FIG. 1. Each patient responded to only a single HLA matched platelet component and were otherwise refractory to all other platelet transfusions (10-120 min posttransfusion CCI <7500) for 21 days. Moreover, both patients were unresponsive to previously administered steroids, Iv IgG, and/or ATG. However, each patient sustained higher average daily platelet counts of $\sim 50 \times 10^9/L$ during and after protein A treatments that were accompanied by excellent responsiveness to both random and HLA matched platelet transfusions with 10-120 min posttransfusion CCI averaging 14,000.

Average daily platelet counts and posttransfusion CCI are summarized for all patients in Table 2. Seven of 12 patients maintained average daily platelet counts two- to ten-fold higher following protein A treatments. These higher platelet counts correlated well with improved posttransfusion CCI for Patients No. 1, 4, and 7 who had average pre-column CCI$\leq 2000$ and post-column CCI$\geq 13,000$. Patient No. 2, although not

TABLE 2

EFFECT OF PROTEIN A COLUMN THERAPY ON PLATELET COUNTS AND POSTTRANSFUSION INCREMENTS

| Patient No. | Prosorba ® Therapy* | Concurrent Therapy | Platelet Pre | Counts Post | Posttransfusion Pre | CCI§ Post |
|---|---|---|---|---|---|---|
| Responders | | | | | | |
| 1 | 6 (off) | None | 17 | 46 | 1610 ± 0 | >13,000 |
| 2 | 1 (off) | CT | 24 ± 9 | 46 ± 18 | 3000 ± 2400 | 6000 ± 2500 |
| 3 | 14 (off) | CT/CSA/IgG | <10 | 100 ± 20 | CI = 1 u/h | CI = 1 u/h |
| 4 | 7 (on) | CSA/CT | 23 ± 12 | 53 ± 21 | 1800 ± 3400 | 14,300 ± 3300 |
| 5 | 12 (on) | None | 13 ± 8 | 100 ± 10 | <1000 | NT** |
| 6 | 6 (off) | CT/IgG | <10 | 51 ± 27 | CI = 2 u/h | CI < 0.5 u/h |
| 7 | 2 (on) | CT | 11 ± 9 | 51 ± 26 | 2000 ± 2900 | 14,000 ± 8000 |
| | | | x = 14 ± 8 | x = 64 ± 25 | x = 1900 ± 700 | x = 11,800 ± 3900 |
| Nonresponders | | | | | | |
| 8 | 1 (off)/5 (on) | CT | <10 | 15 | 0 | 386 ± 460 |
| 9 | 1 (off) | CT/IgG | <10 | <10 | 0 | 0 |
| 10 | 2 (on) | None | 23 ± 8 | 25 ± 9 | 2800 ± 2400 | 5100 ± 3600 |
| 11 | 6 (on) | CT/IgG | <10 | <10 | 0 | 0 |
| 12 | 5 (off) | None | <10 | <10 | 0 | 0 |
| | | | x = 9 ± 8 | x = 11 ± 9 | x = 600 ± 1300 | x = 1100 ± 2200 |

*Form of treatment was either on-line or off-line as indicated in parentheses.
Symbols are the same as listed in Table 1; CT primarily consisted of steroids; CSA, cyclosporine A.
Average best daily posttransfusion platelet count (mean ±sd × $10^9/L$). Pre: as described in Table 1. Post: after protein A column therapy was begun and up to 4 wk following treatment depending on whether the patient was discharged or expired. In some cases, patients were followed 1-12 mo after discharge.
§ Corrected count increment (CCI) based on best average daily platelet count determined at 10-120 min or up to 24 h posttransfusion if earlier measurements were unavailable. Values are means ±sd.
Patients No. 3 and 6 were receiving nearly continuous platelet infusions (CI) so that posttransfusion CCI values could not be determined and instead the rate of infusion is shown.
**No transfusions.
Patient had 10-120 min posttransfusion CCI of 5900 and 3300 after the third and fifth columns, respectively.

Effect of Protein A Column Therapy on Platelet Counts and Post Transfusion CCI The effectiveness of protein A therapy was determined by comparison of pre- and post-treatment platelet counts and response to platelet transfusions using the following criteria:

1) patients with platelets $<10 \times 10^9/L$ had to increase to $<20 \times 10^9/L$ following therapy or patients with platelets between $20-30 \times 10^9/L$ had to increase by at least a factor of two; and achieving clinically significant CCI for 10-120 min ($\geq 7500$), nonetheless experienced a two-fold increase in CCI from 3000 to 6000 following protein A column therapy. Patients No. 3 and 6 had been receiving continuous infusions of platelets before treatment. In Patient No. 6, this declined from 2 units/h to <0.5 unit/h following six column treatments, while in Patient No. 3 there was no change following 14 treatments. The former patient was discharged with a platelet count of $\sim 40 \times 10^9/L$ and at six weeks following her last column treatment was transfusion independent with a platelet count of $116 \times 10^9/L$, while the latter patient expired but had a platelet count of $>100\times10^9/L$ at the time of his death.

Effect of Protein A Column Therapy on Platelet Usage and Platelet Antibody Levels Predictably, increases in platelet counts were generally accompanied by fewer transfusions (Table 3). The 12 patients had been receiving between 4 and 32 units of platelets/day before protein A treatments. Of the seven responders, five had decreased platelet usage of 15-65% after treatment, while two had no change in platelet usage. Of the five nonresponders, Patients No. 10 and 11 experienced a 59% and 47% decrease in platelet usage, respectively.

Platelet Antibody Studies

Serum or plasma was collected from each patient prior to their first protein A column treatment and thereafter following each treatment. Additional serum was collected two weeks after the last column treatment on each surviving patient. Serum was tested for the presence of platelet-reactive antibodies by the monoclonal antibody-specific immobilization of platelet antigens (MAIPA) assay with minor modifications. (D. Christie et al., *Sem. Thrombos. Hemostas.*, in press; V. Kiefel et al., *Blood*, 70:1722 (1987).) In the MAIPA procedure, solubilized platelet antigens are captured in microtiter wells by murine monoclonal antibodies (MoAbs) directed against specific platelet glycoproteins (GPs) or class I antigens for identification of the site to which the patients' antibodies combine. (D. Christie et al., *Sem. Thrombos. Hemostas.*, in press.) Attached human alloantibodies are then detected by a standard ELISA technique and color development monitored at 405 nm with a microplate reader (Biokinetics Reader EL 340, Bio-Tek Instruments, Winooski, Vt.). Relative changes in the levels of circulating antibodies possessed by patients before and after protein A column therapy were determined by comparing the optical densities of serial dilutions of serum samples. Only serum dilutions giving optical densities between 0.5 and 1.5 were used, which is in the linear range of the reader.

Figure 2:
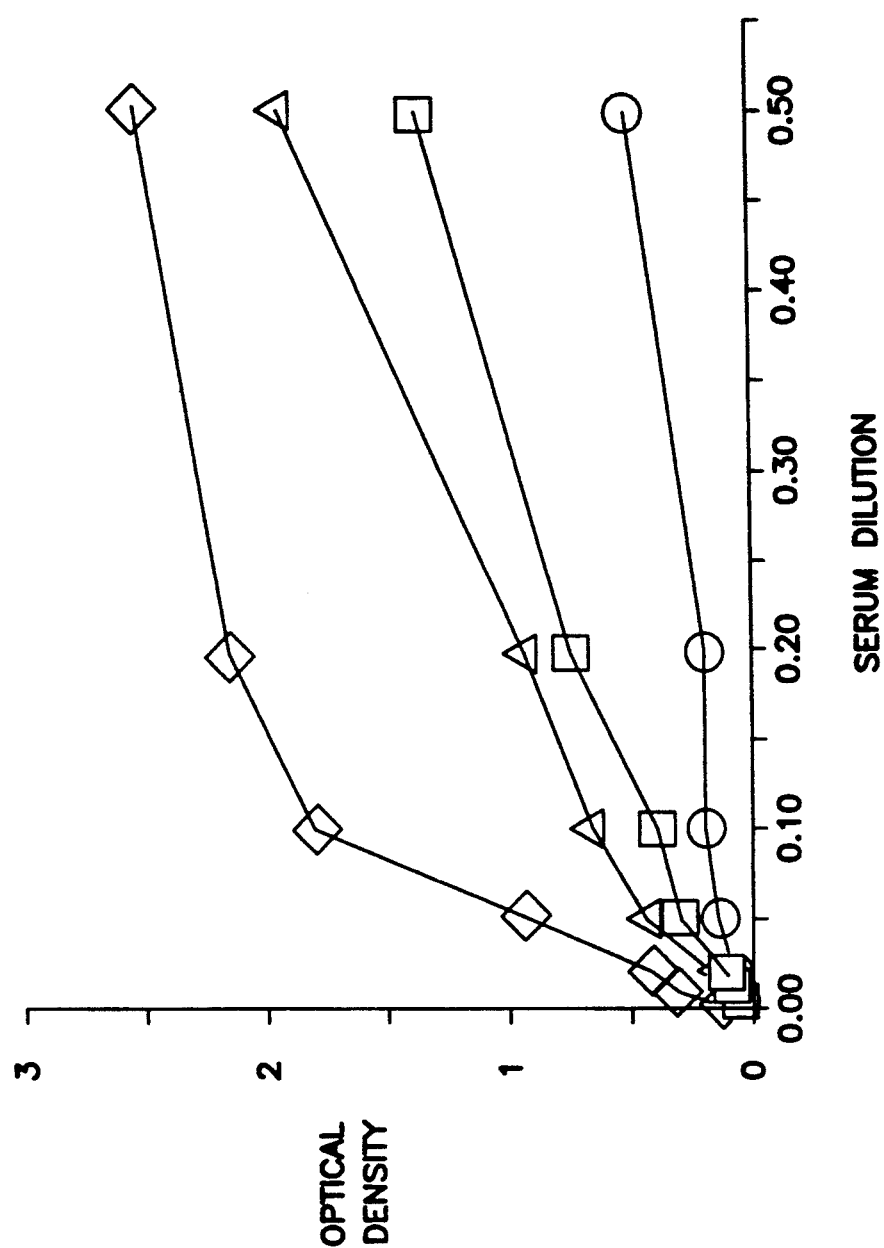
FIG. 2: Antibody titers for Patient No. 5 measured with serum collected prior (closed symbols) to and following (open symbols) 12 protein A column treatments. Antibodies were detected using the MAIPA assay as described in Methods. Antibodies are against HPA-1a (circles) and HPA-3a (squares).

Using the MAIPA assay, the relative amount of antibody present in serum collected immediately before the first treatment and that collected after the last treatment could be determined by comparing titers of the paired serum samples. An example of this is shown for Patient No. 5 in FIG. 2. Among the six responders with detectable platelet antibodies, five demonstrated decreases in circulating platelet antibodies of 65 to >95% following protein A column therapy. One other patient (No. 1) showed a decline of 37% in antibody by lymphocytotoxicity assay, but not by the MAIPA assay (Table 3). Of the four nonresponders with detectable platelet antibodies, Patients No. 8 and 12 had decreases of 75-80% and 40%, respectively.

In addition, sera from some of the patients were tested by immunofluorescence (PIFT) for platelet antibodies (performed by the University of Minnesota Platelet Serology Laboratory) and/or by lymphocytotoxicity (performed by the University of Minnesota Immunology Laboratory) for HLA antibodies. In those patients receiving drugs suspected of causing antibody-mediated platelet destruction, serum was tested for the presence of drug-dependent antibodies by PIFT and the protein A rosette assay, which was performed as previously described. (D. Christie et al., *Blood*, 75:518 (1990) and D. Christie et al., *Transfusion*, 28:322 (1988).)

Alloimmunization to platelet and/or HLA class I antigens was assessed by PIFT, lymphocytotoxicity, and/or the MAIPA assay. Using these methods, sera collected immediately prior to the first protein A column treatment tested positive for platelet-reactive antibodies in all but two patients (Nos. 2 and 10) (Table 1). Seven patients (Nos. 1, 3, 7-9, 10, and 11) had only HLA antibodies, while three had HLA antibodies that were coincident either with anti-A (No. 4), anti-HPA-1a and -3a (No. 5), or anti-GPIIb/IIIa and -GPIb/IX (No. 6). Although the anti-GPIIb/IIIa antibody in Patient No. 6 reacted differentially with platelets typed for HPA-1a, -1b, -3a, -3b, and -4a that are known to reside on GPIIb/IIIa (31-33), no clear specificity(ies) could be discerned. The anti-GPIb/IX antibody appears to have been an autoantibody because it reacted with the patient's own platelets and all other platelets studied.

During the period of thrombocytopenia and RPT, Patients No. 2-5, 7, 9 and 11 and were receiving various medications, including vancomycin, ranitidine, and/or sulfamethoxazole/trimethoprim that are known to be associated with drug-dependent antibody formation. (D. Christie et al., *Blood*, 75:518 (1990); D. Christie et al., *Transfusion*, 28:322 (1988); and P. Ciimo et al., *Am. J. Hematol.*, 2:65 (1977).) By PIFT and/or the protein A rosette assay, no drug-dependent antibodies were detected in the serum of these patients immediately before protein A column therapy.

TABLE 3

EFFECT OF PROTEIN A COLUMN THERAPY ON BLOOD COMPONENT USAGE AND IMMUNOLOGICAL FACTORS

| Patient No. | Platelet Usage* Pre | Platelet Usage* Post | Antibody Reduction ** % |
|---|---|---|---|
| Responders | | | |
| 1 | ~2.6 | ~2.6 | 0 |
| 2 | 5.9 ± 2.7 | 5.0 ± 4.2 | — |
| 3 | 25-30 | 25-30 | >95 (anti-HLA) |
| 4 | 3.9 ± 3.0 | 1.4 ± 2.8 | 65 (anti-HLA) |
| | | | 85 (anti-A) |
| 5 | 1.7 ± 3.9 | NT§ | 85 (anti-HPA-1a) |
| | | | 90 (anti-HPA-3a) |
| | | | 75 (anti-HLA) |
| 6 | 31.6 ± 7.0 | 10.8 ± 5.7 | 60 (anti-GPIb/IX) |
| | | | 90 (anti-GPIIb/IIIa) |
| | | | 80 (anti-HLA) |
| 7 | 12.3 ± 5.5 | 10.5 ± 3.3 | 90 (anti-HLA) |
| Nonresponders | | | |
| 8 | 5.5 ± 1.1 | 5 ± 0 | 80 (anti-HLA) |
| 9 | 12.6 ± 8.9 | 14.5 ± 13 | 0 |
| 10 | 6.4 ± 5.4 | 2.6 ± 2.9 | — |
| 11 | 14.2 ± 3.0 | 7.5 ± 5.1 | 0 |
| | | 15.0 ± 3.2 | |
| 12 | ~5 | ~5 | 40 (anti-HLA) |

**Platelet-specific alloantigens were designated according to the nomenclature recently adopted by the Expert Panel on Serology of the International Society of Blood Transfusion and the International Committee for Standardization in Haematology (Transfusion, 30:477, 1990).

*Units/day (mean ±sd); platelets were either pooled random donor units or platelet concentrates (single random donor or HLA matched) collected by apheresis, which were each counted as 4.7 units.

Based on comparison of antibody titers performed with serum collected before the first protein A column treatment with that collected immediately after the last treatment.

Patient had no detectable change in HLA antibodies as measured in the MAIPA assay; however, by lymphocytotoxicity assay the patient's serum reacted with 25/48 cells before protein A treatment and 16/48 cells after treatment.

§No transfusions.

Platelet usage for protein A column treatments #1-5 (top line, 11 days) and beginning the day after the 5th column treatment until the patient expired (bottom line, 18 days). On the day after the 5th column treatment the patient fell and hit his head; the increased platelet usage was a precautionary measure against possible intracranial hemorrhage.

Side Effects Associated with Protein A Column Therapy

Previously reported side effects (e.g. chills, urticaria, dyspnea, and hypotension) associated with protein A column therapy occurred in 4 of the 12 patients (Nos. 3, 5, 10 and 12). (T. Guthrie et al., *Sem. Hematol.*, 26(Suppl 1):3 (1989) and A. Mittleman et al., *Sem. Hematol.*, 26(Suppl 1):15 (1989).) Patient No. 3 developed mild nausea during four of 14 treatments and mild chills/fever during one treatment. Patient No. 5 experienced some hypotension in association with the first column treatment, but no further problems were encountered with five additional treatments. Two months later the patient received an additional six protein A treatments and experienced mild hypotension and dermatologic reactions that did not prevent completion of therapy. Patient No. 10 elected to discontinue therapy after two treatments following the development of a rash. Patient No. 12 experienced one mild episode of dyspnea during her first column treatment, but completed four subsequent treatments with no further complications. None of the side effects observed in these patients were life-threatening.

The references are incorporated by reference herein. The invention has been described with reference to various specific and preferred embodiments and techniques. However, it should be understood that many variations and modifications may be made while remaining within the spirit and scope of the invention.

What is claimed is:

1. A therapeutic method for treating refractoriness to platelet transfusion due to alloimmunization, comprising:
   (a) isolating a portion of blood serum from an alloimmunized patient undergoing platelet transfusion therapy;
   (b) passing the portion of serum through a bed comprising Staphylococcal protein A coupled to a finely divided solid support, so that IgG and IgG-associated immune complexes are removed from the serum, to yield a portion of treated plasma; and
   (c) returning said portion of treated plasma to said patient to achieved an increase in average daily platelet counts over pretreatment levels for at least one week posttransfusion.

2. The method of claim 1 wherein said alloimmunized patient suffers from leukemia, aplastic anemia, myelofibrosis, myelodysplasia or is a bone marrow transplant patient.

3. The method of claim 1 wherein the bed is contained within a chromatography column.

4. The method of claim 1 wherein about 500–2500 ml of plasma is passed through the bed and returned to the patient.

5. The method of claim 1 wherein, in step (a), the portion of plasma is isolated by withdrawing serial units of blood from the patient, centrifuging the serial units of blood to separate the cellular portion from the plasma, pooling the plasma, and returning the cellular component to the patient.

6. The method of claim 1 wherein the solid support is silica gel.

7. The method of claim 1 wherein steps (a) to (c) are performed continuously, so that a stream of blood is withdrawn from the patient in step (a), and a stream of treated plasma is returned to the patient in step (c).

* * * * *

UNITED STATES PATENT AND TRADEMARK OFFICE
CERTIFICATE OF CORRECTION

PATENT NO. : 5,277,701

DATED : January 11, 1994

INVENTOR(S) : Christie et al.

It is certified that error appears in the above-identified patent and that said Letters Patent is hereby corrected as shown below:

On the title page, item [54] Title, "ALUIMMUNIZATION" should read --ALLOIMMUNIZATION--.

Title page, Item [56]: Other Publications, in Christie et al. "platlelet" should read --platelet--.

item [57] Abstract, "staphococcal" should read --staphylococcal--.

Page 2, Other Publications in Cimo et al., "platellet" should read --platelet--

Page 2, Other Publication in Daly et al., "therap" should read --therapy--.

Page 2, Other Publications in Gurthrie, et al., "Gurthrie" should read --Guthrie--.

Page 2, Other Publication in Kickler et al., "pateints" should read --patients--.

Page 2, Other Publications, column 2, in Langenscheidt et al., "*transfusion*" should read --*Transfusion*--.

Page 2, Other Publications, column 2, in Litzow et al., "a plastic" should read --aplastic--.

Page 2, Other Publications, column 2, in van Marwijk et al., "trail" should read --trial--.

UNITED STATES PATENT AND TRADEMARK OFFICE
CERTIFICATE OF CORRECTION

PATENT NO. : 5,277,701
DATED : January 11, 1994
INVENTOR(S) : Christie et al.

It is certified that error appears in the above-identified patent and that said Letters Patent is hereby corrected as shown below:

Column 1, line 67, "RTP" should read --RPT--.

Column 2, line 22, "RTP" should read --RPT--.

Column 5, line 34, "antigens" should read --antibodies--.

Column 6, line 23, "manage-" should read --manage--.

Column 6, line 4 of TABLE 1, insert --†-- after the word "Clinical" and insert --‡-- after the word "Count".

Column 6, line 5 of TABLE 1, insert --¶-- after the word "Specificity".

Column 7, line 4 of TABLE 1, insert --†-- after the word "Clinical" and insert --‡-- after the word "Count".

Column 7, line 5 of TABLE 1, insert --¶-- after the word "Specificity".

Column 7, line 13 of TABLE 1, insert --†-- before the word "Seven".

Column 7, line 15 of TABLE 1, insert --‡-- before the word "Average".

Column 7, line 20 of TABLE 1, insert --¶-- before the word "Platelet".

UNITED STATES PATENT AND TRADEMARK OFFICE
CERTIFICATE OF CORRECTION

PATENT NO. : 5,277,701

DATED : January 11, 1994

INVENTOR(S) : Christie et al.

It is certified that error appears in the above-identified patent and that said Letters Patent is hereby corrected as shown below:

Column 8, line 43, "sale" should read --saline--.

Column 9, line 66, "<" should read -->--.

Column 9, line 4 of TABLE 2, insert --†-- after the word "Concurrent". Column 9, line 5 of TABLE 2, insert --‡-- after the word "Counts".

Column 9, line 23 of TABLE 2, insert --†-- before the word "Symbols".

Column 9, line 24 of TABLE 2, insert --‡-- before the word "Average".

Column 9, line 29 of TABLE 2, insert --¶-- before the word "Patients".

Column 9, line 32 of TABLE 2, insert --††-- before the word "Patient".

Column 10, line 9 of TABLE 2, insert --¶-- after the letters "CI".

Column 10, line 18 of TABLE 2, insert --††-- after the numeral "0" in last column of table.

UNITED STATES PATENT AND TRADEMARK OFFICE
CERTIFICATE OF CORRECTION

PATENT NO. : 5,277,701

DATED : January 11, 1994

INVENTOR(S) : Christie et al.

It is certified that error appears in the above-identified patent and that said Letters Patent is hereby corrected as shown below:

Column 10, TABLE 2, the headings for table columns 4 and 5, "Platelet Pre" and "Counts Post", should read --Pre-- and --Post--, respectively. A heading over both table columns 4 and 5 should read --Platelet Counts‡--.

Column 10, TABLE 2, the headings for table columns 6 and 7, "Posttransfusion Pre" and "CCI§ Post", should read --Pre-- and --Post--, respectively. A heading over both table columns 6 and 7 should read --Posttransfusion CCI§--.

Column 12, line 21, delete "and".

Column 12, line 36 of TABLE 3, "Antibody Reduction %" should read --Antibody Reduction †%--.

Column 12, line 39 of TABLE 3, insert --‡-- after the numeral "0".Column 12, line 51 of TABLE 3, "5.5" should read --5.4--.

Column 12, line 53 of TABLE 3, insert --¶-- after the numeral "5.1".

Column 12, line 54 of TABLE 3, insert --¶-- after the numeral "3.2".

Column 12, line 65 of TABLE 3, insert --†-- before the word "Based".

UNITED STATES PATENT AND TRADEMARK OFFICE
CERTIFICATE OF CORRECTION

PATENT NO. : 5,277,701

DATED : January 11, 1994

INVENTOR(S) : Christie et al.

It is certified that error appears in the above-identified patent and that said Letters Patent is hereby corrected as shown below:

Column 12, line 68 of TABLE 3, insert --‡-- before the word "Patient". Column 12, line 72 of TABLE 3, insert --¶-- before the word "Platelet".

Column 12, line 76 of TABLE 3, insert --.-- after the word "hemorrhage".

Column 14, line 10, "achieved" should read --achieve--.

Signed and Sealed this

Twenty-ninth Day of November, 1994

Attest:

BRUCE LEHMAN

Attesting Officer     *Commissioner of Patents and Trademarks*